United States Patent [19]

Vaillancourt

[11] Patent Number: 5,368,801
[45] Date of Patent: Nov. 29, 1994

[54] METHOD OF MOUNTING A SEPTUM IN A CONNECTOR

[75] Inventor: Michael Vaillancourt, Livingston, N.J.

[73] Assignee: VLV Associates, East Hanover, N.J.

[21] Appl. No.: 650

[22] Filed: Jan. 5, 1993

[51] Int. Cl.⁵ .................. B29C 65/18; A61M 5/00
[52] U.S. Cl. ................. 264/249; 264/297.8; 264/322; 264/339; 264/259; 604/905
[58] Field of Search ............ 264/248, 249, 322, 296, 264/297.8, 259, 339; 604/86, 283, 905

[56] References Cited

U.S. PATENT DOCUMENTS

| | | | |
|---|---|---|---|
| 4,219,912 | 9/1980 | Adams | 604/86 |
| 4,294,249 | 10/1981 | Sheehan et al. | 604/86 |
| 4,551,292 | 11/1985 | Fletcher et al. | 264/322 |
| 4,735,311 | 4/1988 | Lowe et al. | 264/296 |
| 4,874,369 | 10/1989 | Kulle et al. | 604/86 |
| 5,126,090 | 6/1992 | Egolf et al. | 264/249 |

FOREIGN PATENT DOCUMENTS 3031242  3/1982  Germany .................. 604/86

*Primary Examiner*—Mathieu Vargot
*Attorney, Agent, or Firm*—Francis C. Hand

[57] ABSTRACT

The method of mounting a disc-shaped septum within a connector includes a step of deforming a thin annular wall at the end of the connector into a curled over shape so as to secure the septum in place. Curling over of these wall occurs under heat energy which is applied only to the end of the connector without heating of the main body of the connector. Deformation of the thin end wall of the connector causes an outward bulging of a peripheral edge of the connector as well as bulging of the opposite ends of the connector into a domed shape.

15 Claims, 1 Drawing Sheet

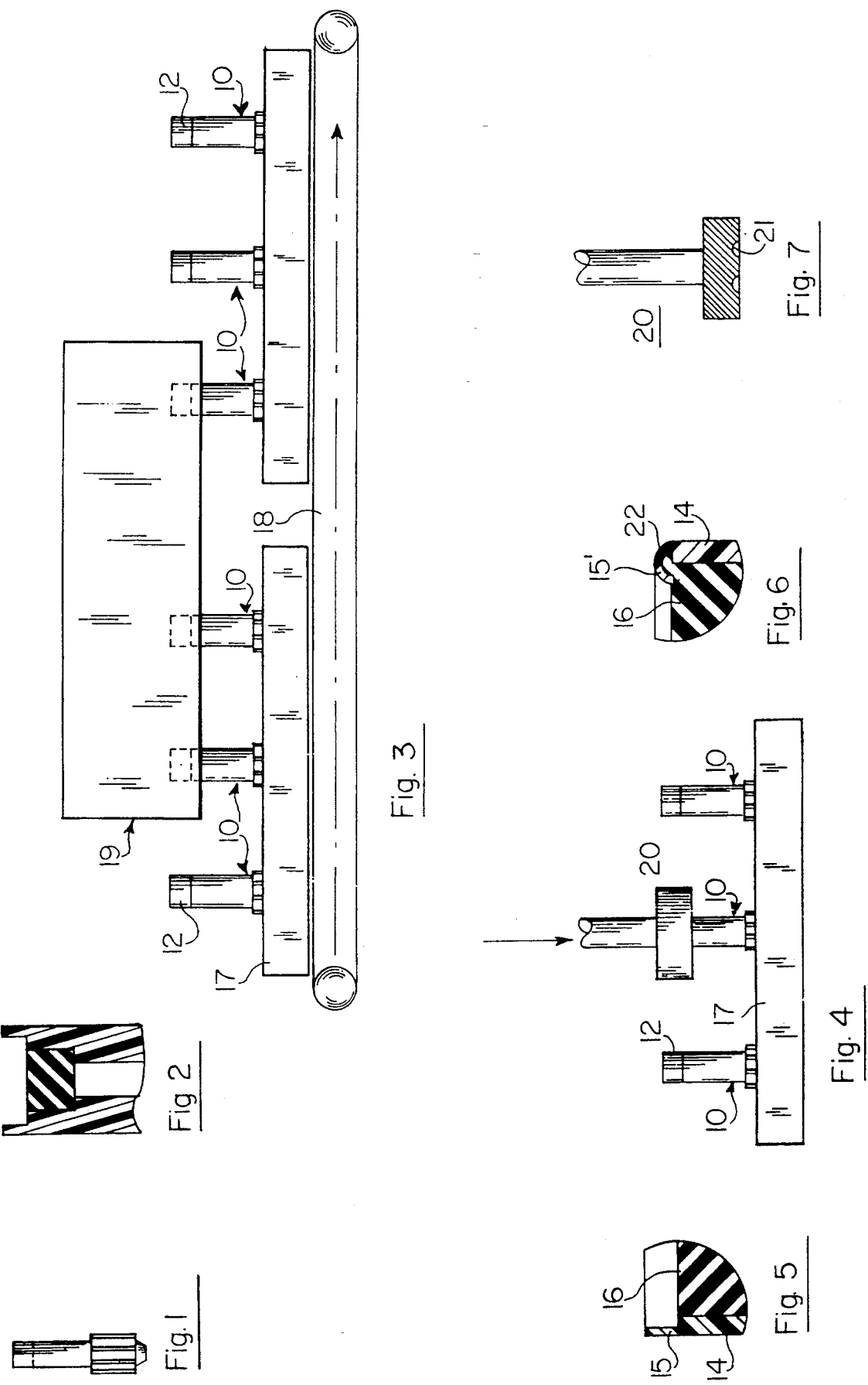

METHOD OF MOUNTING A SEPTUM IN A CONNECTOR

BACKGROUND OF THE INVENTION

This invention relates to a method of mounting a septum in a connector.

As is known, various types of connectors have been used in connector assemblies in order to conduct a fluid, for example, as described in U.S. Pat. No. 4,511,359. In some cases, the connector assemblies have been employed for connecting a line from an intravenous fluid pack to a IV administration set connected to the vein of a patient. Generally, the connector assemblies have employed two interfitting connectors, i.e. a male connector and a female connector which, when mated, form a connection from one tubing to another and which when disconnected separate the tubings. In some cases, the female connector has been fitted with a hollow needle while the male connector is fitted with a septum which can be pierced by the hollow needle when a connection is being made.

In the past, various techniques have been known for mounting a septum on a connector. For example, in some cases, the septum has been in the form of a rubber sleeve which can be mounted over the open end of a connector, such as described in U.S. Pat. No. 4,752,292, or to cover both the interior and exterior wall surface of a connector, such as described in U.S. Pat. No. 5,139,483. In either case, the rubber sleeve may be held in place, for example, by a shrink band. However, there is a risk that a patient may manipulate the septum when the connector end is exposed, such as after a disconnect has been made from a mating female connector. As a result, the septum may break free from the connector. To avoid this, glue has been employed to hold the septum in place. However, septums of this type have generally not permitted multiple uses. That is, where a hollow needle such as an 18 gauge is used, leakages have occurred through the body of the septum where the needle has been used more than twice to pierce through the septum.

Another technique is to form the septum as a cap which can be fitted onto the end of a male connector as described in U.S. Pat. No. 4,950,260 or as described in U.S. Pat. No. 4,981,469, to form the septum as a cap with a disc-like section and two annular sections extending from the disc-like section to fit over an open end of an adapter.

Still another technique which has been known is the use of a rubber disc which can be fully mounted within the end of a connector. In such cases, the rubber disc has been mounted in a recessed end of the connector and the end of the connector crimped or otherwise deformed such as by use of ultrasound in order to maintain the rubber disc in place. However, such techniques have been relatively expensive and, in some cases, may have a detrimental effect in the connector.

It is also known to heat the end of a connector above the melting point to carry out a deformation step. For example, where the connector is made of a polycarbonate plastic, the melting point is about 550° F. However, this amount of heat can cause damage to the rubber disc as well as the remainder of the connector.

BRIEF SUMMARY OF THE INVENTION

Accordingly, it is an object of the invention to provide a relatively simple process for the mounting of a septum in a connector.

It is another object of the invention to provide a reliable process for mounting a septum in a male connector without damaging the connector.

It is another object of the invention to provide a minimum of heat to mount a rubber septum in a recessed end of a plastic connector.

Briefly, the invention provides a method of mounting a septum in a connector which includes the steps of obtaining a connector having a predetermined heat distortion temperature and an end with a first cylindrical wall of predetermined inner diameter and coaxial second wall of an inner diameter less than the first wall and mounting a septum within the first cylindrical wall. In accordance with the invention, the second wall of the connector is heated to the predetermined heat distortion temperature which is significantly below the melting point of the material of the connector, for example, where the connector is made of a polycarbonate with a melting point of 550° F., the heat distortion temperature is in the range of from 270° F. to 290° F. The connector end is thereafter deformed under a longitudinally applied compressive force in order to effect a radially inward curling of the second wall sufficient to secure the septum in place.

The method may be carried out in a batch manner or in a continuous manner. That is, a number of connectors may be provided with septums, heated and then deformed in a batch manner. Alternatively, a series of connectors may be conveyed through a suitable oven or heating means in order to heat the ends of the connectors prior to deformation, for example, in a sequential manner by a suitable die or deforming means.

The method is carried out so that only the end of the connector in which the rubber septum is mounted requires heating. Accordingly, a minimum of heat energy can be used in order to carry out the deformation of the end of the connector over the rubber septum. Furthermore, by only heating the end of the connector, the remainder of the connector remains substantially unheated so that the remainder of the connector is able to withstand relatively large deformation forces which are imposed coaxially on the connector when the end of the connector is being deformed.

BRIEF DESCRIPTION OF THE DRAWINGS

These and other objects and advantages of the invention will become more apparent in the following detailed description taken in conjunction with the accompanying drawings herein:

FIG. 1 illustrates a side view of a connector employed in accordance with the invention;

FIG. 2 illustrates an enlarged cross-sectional view of a septum-receiving end of the connector of FIG. 1;

FIG. 3 illustrates a schematic arrangement for a system for heating a series of connectors in accordance with the invention;

FIG. 4 illustrates a deforming means for deforming a free end of a connector in accordance with the invention;

FIG. 5 illustrates a part cross-sectional view of a heated end of a connector prior to deformation;

FIG. 6 illustrates a part cross-sectional view of a deformed end of a connector in accordance with the invention; and FIG. 7 illustrates a part cross-sectional view of a die used for the deformation of a connector in accordance with the invention.

DETAILED DESCRIPTION OF THE INVENTION

Referring to FIG. 1, a male connector 10 of tubular construction is made of a plastic material, such as a polycarbonate, and is provided with a tubular extension 11 or a female luer connection (not shown) at one end and a heat deformable hollow tubular end 12 at the opposite end, i.e. the upper end as viewed. The connector 10 is sized so as to be telescopically fitted with a female connector (not shown) of a connector assembly, for example, a female connector having a hollow needle.

As indicated in FIG. 2, the tubular end 12 of the connector 10 includes an inner annular shoulder which defines an annular abutment surface 13 and a first cylindrical wall 14 which extends longitudinally from the abutment surface 13. In addition, the tubular end 12 has a second cylindrical wall 15 extending from the first wall 14. As indicated, this second wall 15 has a greater inner diameter than the first wall 14. That is to say, the second wall 15 is thinner than the first wall 14.

In addition, as indicated in FIG. 2, a septum 16 of disc shape, for example, a rubber plug, is disposed in the end of the connector 10 against the abutment surface 13 and in slide fit relation to the first cylindrical wall 15. As indicated, this septum 16 is of a longitudinal length which is equal to the longitudinal length of the first wall 14.

Referring to FIG. 3, in order to secure the rubber septum 16 within the tubular end 13 of the connector 10, a plurality of connectors 10, each of which has been fitted with a septum, are mounted in a suitable fixture 17 and conveyed along a conveyor belt 18 of a conveyor for passage through a heating oven 19. As indicated, only the upper end of each connector 10 is exposed to the heat generated within the heating oven 19. For example, each end 12 of a tubular connector 10 made of polycarbonate is heated to a temperature significantly below the melting point of the plastic, that is to a range of from 270° F. to 290° F. with a preferred range of 280° plus or minus 5° F. In addition, the length of time that each connector 10 remains exposed to the heat of the oven 19 is in a range of time from about 6 minutes to 10 minutes with a preferred time of approximately 8 minutes for a deformable wall thickness of 0.016"; whereas for a deformable wall thickness of 0.012" the preferred time is 5 minutes.

Referring to FIG. 4, after the end 12 of a connector 10 has been heated to a suitable temperature, the connector 10 while still mounted on the fixture 17 is moved to a deforming station under a die 20 which is formed with an annular groove 21 (see FIG. 7) of semi-circular cross-section or any other suitable curved cross-section. The die 20 and connector 10 are then moved relative to each other, i.e. the die 20 moves downwardly in the direction indicated by the arrow so that the groove 21 receives the end of the connector 10 while the die 20 imposes a force on the heated end 12 of the connector 10 which is directed coaxially of the connector 10 as the die 20 continues to move the groove 21 causes the thin heated cylindrical wall 15 of the connector 10 to curl radially inwardly from a cylindrical shape as shown in FIG. 5 into a shape conforming to the groove 21, that is, into an oval shape, as indicated in FIG. 6.

Referring to FIG. 6, the deformed wall 15' of the connector 10 curls inwardly on itself to an extent sufficient to secure the septum 16 in place. In addition, deformation of the wall 15 causes a peripheral end portion 22 of the septum 16 to bulge outwardly into an annular space defined within the curled wall 15' of the connector 10. Still further, deformation of the wall 15 effects a deformation of a central end portion of the septum 16 into a domed shape coaxially within the curled wall 15'.

After deformation of the end of the connector 10, the die 20 is moved relative to the connector 10, i.e. upwardly as viewed, and the connector is subsequently cooled and passed to another station for other purposes.

Alternatively, other techniques may be used for the heating of the end of a connector. Further, although the heating and deformation steps are described as taking place sequentially, these two steps may overlap so that heating and deformation may take place, at least in part, simultaneously.

It is to be noted that heating of only the end 12 of the connector 10 allows the remainder of the connector 10 to remain substantially unheated and well below the heat distortion temperature of the plastic. Thus, a substantial deformation force can be imposed upon the end 12 of the connector 10 by the die 20 since the remainder of the connector 10 is able to withstand a relatively large compressive force. For example, if the entire connector 10 were heated, the die 20 could well cause a bulging out of the remainder of the connector 10. This, in turn, would result in a distorted shape to the connector and may well prevent the male connector 10 from fitting into a female connector of a connector assembly.

Further, it has been found that the thickness of the thicker cylindrical wall 14 of the connector 10 provides column strength to prevent buckling of the connector end 12 under the forces imposed by the die 20. In this respect, the thicker cylindrical wall 14 supports the septum 16 radially for day-to-day use. Further, without distorting, the cylindrical nature of the wall 14 provides for a permanent seal between the septum 16 and the wall 14. Of note, due to the compression of the septum 16 during deformation of the thinner cylindrical wall 15, the septum 16 tends to bulge radially outwardly so as to effect a better seal between the septum and the cylindrical wall 14.

The thinness of the second wall 15 of the connector is such as to permit ready deformation under the heat and pressure forces. Further, deformation of this wall 15 serves to impart an axially directed bulge in the septum 16 at both ends. This, in turn, enhances the self-sealing effect of the septum 16 when a needle is withdrawn from the septum 16.

It has been found that the septum 16 may reseal many times in a reliable manner after multiple passages of a hollow needle (not shown). This is due in part to the relatively large "land" length of the septum 16 against the cylindrical wall 14, for example, a land length of 0.230". In addition, it has been found that for relatively large bore hollow needles of ⅛" diameter, the septum 16 may take four or five sticks before leaking.

It has been found that if too much heat is applied to a connector 10, the whole connector 10 bulges radially outward and cannot fit into a compatible female connector to form a connection. On the other hand, if there is insufficient heat imparted to the connector 10, the connector 10 is unduly stressed and tends to crack under a "plier test", that is under a pinching in of the end 12 of the connector 10 from a cylindrical shape to an oval shape.

By the application of sufficient heat in accordance with the above described process, the connector 10 remains resilient under the "plier test", that is, the part is not unduly stressed even though the connector 10 was post formed after molding and can be deformed to an oval shape without cracking or crazing. Further, by heating only the end 12 of the connector 10 containing the rubber septum 16 to a temperature significantly below the melting point of the material of the connector 10, a minimum of heat energy is required to mount the septum 16 in place. The "plier test" has been found to correlate with field conditions i.e. when the part cracks under this test, it will fail in the field either immediately after a period of time. Hence, the value of this test.

In one embodiment of the method, a sub-assembled connector 10 of polycarbonate can be mounted in a fixture 17 with the septum 16, for example, in the form of a latex rubber disc, slidably mounted in place. The fixture 17 is then conveyed via the conveyor belt 18 under the over 19 which has been preheated to 270° F. so that the end 12 of the connector 10 is exposed to heat for a minimum of ten minutes. Thereafter, the fixture 17 is removed from under the oven 19 and placed on a forming press (not shown) in which one or more dies 20 are suitably mounted. The die 20 is then brought to bear on each connector 10 in order to deform the heated end of the connector 10 as described above.

The invention thus provides a method of mounting a septum of disc shape in a hollow end of a connector in a relatively simple and reliable manner.

Further, the invention provides a method of mounting a rubber septum within a plastic connector made of polycarbonate using a heat deformation process which does not detrimentally effect the shape or structural integrity of the connector.

The invention further provides a process for mounting a septum within a connector without deformation of the connector from a cylindrical shape.

What is claimed is:

1. A method of mounting a septum in a connector, said method comprising the steps of
   obtaining a connector having a predetermined heat distortion temperature and a heat deformable hollow tubular end including an inner annular shoulder defining: an annular abutment surface and a first cylindrical wall extending longitudinally from said abutment surface, said end further including a second cylindrical wall extending from said first wall and having a greater inner diameter than said first wall;
   mounting a septum of disc shape in said end of said connector against said abutment surface in slide fit relation to said first cylindrical wall;
   heating at least said second wall of said connector to a said predetermined heat distortion temperature; and
   thereafter deforming said heated second wall under a longitudinally applied force to effect a radially inward curling of said second wall sufficient to secure said septum in place.

2. A method as set forth in claim 1 wherein said second wall is curled into an semi-oval cross-sectional shape.

3. A method as set forth in claim 2 wherein deformation of said second wall deforms a peripheral end portion of said septum outwardly into an annular space defined within said second wall.

4. A method as set forth in claim 3 wherein said step of deforming said second wall effects a deformation of a central portion of said septum into a domed shape coaxially within said second wall.

5. A method as set forth in claim 1 wherein deformation of said second wall deforms a peripheral end portion of said septum outwardly into an annular space defined within said curled second wall.

6. A method as set forth in claim 1 wherein said step of deforming said second wall effects a deformation of a central portion of said septum into a domed shape coaxially within said second wall.

7. A method as set forth in claim 1 wherein said predetermined heat distortion temperature is within a range of from 270° F. to 290° F.

8. A method as set forth in claim 1 wherein said step of heating effects heating of said second wall at said predetermined heat distortion temperature for a preset time.

9. A method as set forth in claim 8 wherein said preset time is from 66 minutes to 10 minutes.

10. A method as set forth in claim 1 wherein said heating and deforming steps are performed sequentially in a continuous process.

11. A method as set forth in claim 1 wherein said septum is made of rubber and said connector is made of polycarbonate plastic.

12. A method of mounting a septum in a connector, said method comprising the steps of
   obtaining a plastic connector having an end with a first cylindrical wall of predetermined inner diameter and a coaxial second wall of an inner diameter less than said first wall;
   mounting a septum within said first cylindrical wall;
   heating at least said second wall of said connector to a predetermined temperature range of from 270° F. to 290° F.; and
   thereafter deforming said heated second wall under a longitudinally applied force to effect a radially inward curling of said second wall sufficient to secure said septum in place.

13. A method as set forth in claim 12 wherein said second wall causes a peripheral end portion of said septum to bulge outwardly into an annular space defined within said second wall during deformation of said second wall.

14. A method as set forth in claim 13 wherein said step of deforming said second wall effects a deformation of a central portion of said septum into a domed shape coaxially within said curled second wall.

15. A method as set forth in claim 13 wherein said second wall is curled into an semi-oval cross-sectional shape.

* * * * *

UNITED STATES PATENT AND TRADEMARK OFFICE
CERTIFICATE OF CORRECTION

PATENT NO. : 5,368,801
DATED : November 29, 1994
INVENTOR(S) : MICHAEL VAILLANCOURT It is certified that error appears in the above-indentified patent and that said Letters Patent is hereby corrected as shown below:

```
Column 5, line 60 cancel "said"
Column 6, line 30 change "66 minutes" to -6 minutes-
Column 6, line 42 change "less" to -greater-
```

Signed and Sealed this

Second Day of May, 1995

Attest:

BRUCE LEHMAN

*Attesting Officer*   Commissioner of Patents and Trademarks